United States Patent [19]

Scott-Kestin et al.

[11] Patent Number: 4,679,430
[45] Date of Patent: Jul. 14, 1987

[54] ULTRASONIC LIQUID INTERFACE DETECTOR

[75] Inventors: Colin B. Scott-Kestin, Stoke-sub-Hamdon; Roger B. Pike, Newbury; Roger D. Watkins, Wantage; Arthur B. Gillespie, Abingdon; Michael O. Deighton, Reading, all of England

[73] Assignee: United Kingdom Atomic Energy Authority, London, England

[21] Appl. No.: 593,277

[22] Filed: Mar. 26, 1984

[30] Foreign Application Priority Data

Mar. 30, 1983 [GB] United Kingdom ............. 8308813

[51] Int. Cl.$^4$ .................................... G01F 23/22
[52] U.S. Cl. .................................. 73/290 V; 73/599; 340/621
[58] Field of Search ............... 73/290 V, 579, 599, 73/DIG. 1, 644; 331/155; 367/908; 340/621; 181/400

[56] References Cited

U.S. PATENT DOCUMENTS

| | | | |
|---|---|---|---|
| 3,019,650 | 2/1962 | Worswick | 73/290 V |
| 3,079,596 | 2/1963 | Atkinson | 73/290 V |
| 3,295,629 | 1/1967 | Papadakis | 181/400 |
| 3,512,400 | 5/1970 | Lynnworth | 73/599 |
| 3,520,186 | 7/1970 | Adams et al. | 73/290 V |
| 4,118,983 | 10/1978 | Brazhnikov | 340/621 |
| 4,182,177 | 1/1980 | Prough | 73/290 V |
| 4,213,337 | 7/1980 | Langdon | 340/621 |
| 4,280,126 | 7/1981 | White | 340/621 |
| 4,320,659 | 3/1982 | Lynnworth et al. | 73/290 V |

FOREIGN PATENT DOCUMENTS

| | | | |
|---|---|---|---|
| 0131080 | 11/1978 | Japan | 73/579 |
| 1555549 | 11/1979 | United Kingdom . | |
| 2054853 | 2/1981 | United Kingdom | 73/290 V |

Primary Examiner—Charles Frankfort
Assistant Examiner—Patrick R. Scanlon
Attorney, Agent, or Firm—William R. Hinds

[57] ABSTRACT

A sensor for detecting an interface of a liquid in a container comprises a transmitter and a receiver of ultrasonic waves, each situated outside the container, and coupled to the wall of the container by a strip waveguide. The transmitter is arranged to cause surface acoustic waves to propagate through a portion of the wall, and the receiver is arranged to detect waves derived from the transmitter. When the liquid is adjacent to the portion of the wall, mode conversion of the surface acoustic waves in the wall of the vessel into compression waves in the liquid causes a change in the energy of waves reaching the receiver.

8 Claims, 5 Drawing Figures

ULTRASONIC LIQUID INTERFACE DETECTOR

This invention relates to devices and a method for detecting an interface of a liquid in a container by ultrasonic means.

As is described in UK Patent Application No. 2 019 568 A, the level of liquid in a tank may be determined ultrasonically by means of a dipstick including a wave guide dipping into the liquid and an associated reflector for ultrasonic waves in the liquid. Such a device need have no moving parts, but is an invasive device. For many purposes a non-invasive liquid level detector, all of whose components were situated outside the tank, would be advantageous.

UK Patent Specification No. 1 555 549 describes a liquid level detector comprising an emitter and a receiver of acoustic waves mounted on a wall of a container, the emitter being arranged to cause vibrations such as Lamb waves to propagate transverse to the wall thickness and the receiver being arranged to sense the vibrations. The presence of a liquid adjacent to the wall is indicated by a decrease in the amplitude of the received waves, the amplitude attenuation being dependant upon the acoustic impedance of the liquid. Although this detector is non-invasive, it is not suitable for situations in which the direct application of transducers to a wall of a container is inconvenient or unacceptable, such as where the liquid is hot or radioactive; nor is it applicable where the wall is curved.

According to the present invention, there is provided a sensor to detect an interface of a liquid in a container for containing the liquid, comprising a first ultrasonic transducer situated outside the container and arranged to cause Lamb waves of predetermined wavelength to propagate through a portion of a wall of the container, a second ultrasonic transducer situated outside the container and arranged to detect Lamb waves propagating through the portion of the wall and to produce an electrical signal related to the amplitude thereof, and indicating means responsive to the electrical signal from the second transducer to provide an indication of an interface of the liquid within the container, wherein the first ultrasonic transducer and the second ultrasonic transducer are acoustically coupled to the wall by respective strip waveguides along which Lamb waves propagate, only an end of each waveguide contacting the wall thereby separating the transducers from the wall of the container.

The interface may be an interface between a liquid and a gas, or between two immiscible liquids. A Lamb wave is an acoustic wave in which the wavelength of the wave is comparable with the thickness of the body in which it is travelling. By the term strip waveguide is meant a strip of material whose thickness is much less than its breadth, along which a Lamb wave may be transmitted. Preferably the thickness of the strip waveguide is less than half the wavelength of the Lamb waves which are to propagate through the wall.

An alternative form of sensor further comprises a third ultrasonic transducer situated outside the container for causing Lamb waves of predetermined wavelength to propagate through a second portion of the wall lower than the first mentioned portion; a fourth ultrasonic transducer situated outside the container for detecting Lamb waves propagating through the second portion of the wall and for producing an electrical signal related to the amplitude thereof; and means for exciting the first and the third ultrasonic transducer; the third ultrasonic transducer and the fourth ultrasonic transducer being acoustically coupled to the wall by respective strip waveguides along which Lamb waves propagate, only an end of each waveguide contacting the wall; and the indicating means being responsive to the signals from both the second and the fourth ultrasonic transducer for providing an indication of the interface.

Also according to the invention there is provided a method for detecting an interface of a liquid in a container comprising, causing Lamb waves to propagate through a portion of a wall of the container, receiving the Lamb waves after they have propagated through the portion of the wall, and detecting the liquid interface in response to the amplitude of the received Lamb waves, wherein the Lamb waves are transmitted to and from the portion of the wall as Lamb waves propagating along respective strip waveguides, only an end of each waveguide contacting the wall thereby separating transmitting and receiving transducers of the propagated Lamb waves from the wall of the container.

Whenever a Lamb wave propagates in a solid surface which is in contact with a liquid then mode conversion of the waves occurs: the Lamb wave in the surface loses energy, while an ultrasonic compression wave is caused to propagate through the liquid. The interface of the liquid may therefore be detected by detecting the decrease in energy and amplitude of the Lamb wave in the wall of the container.

The invention will now be further described by way of example only and with reference to the accompanying drawings, in which.

Figure 1:
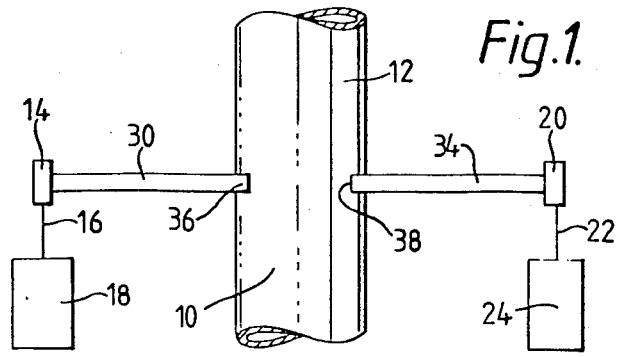
FIG. 1 shows diagrammatically a liquid interface sensor embodying the invention.

In FIG. 1 a liquid interface sensor is shown attached to the outside of a wall 10, 2.7 mm thick, of a container 12 (shown as a pipe) for a liquid. The sensor comprises a piezoelectric transmitter transducer 14 connected by an electric cable 16 to a signal generator 18, and a piezoelectric receiver transducer 20 connected by an electric cable 22 to a signal detector 24.

The transmitter transducer 14 is attached to one end of a stainless steel strip 30, 25 mm wide and 1.6 mm thick, the other end 36 of the strip 30 being welded to the outside of the wall 10, and the receiver transducer 20 is attached to one end of a second stainless steel strip 34 also 25 mm wide and 1.6 mm thick, the other end 38 of which is also welded to the outside of the wall 10 at the same horizontal level but angularly displaced from the end 36 of the strip 30.

When the signal generator 18 is energised the transmitter transducer 14 oscillates at 1 MHz and causes a Lamb wave to propagate along the strip 30, thereby generating a Lamb wave in the adjacent portion of the wall 10. A Lamb wave propagating through the wall 10 at the end 38 of a second stainless steel strip 34 will generate a Lamb wave in the strip 34 which will be received by the receiver transducer 20. The steel strips 30 and 34 thus act as waveguides to transmit the Lamb waves to and from the wall 10 of the container 12, respectively.

If the level of the liquid in the container 12 is below the horizontal level of the ends 36 and 38 of the strips 30 and 34 then the wave detected by the receiver transducer 20 has an amplitude A. If the level of the liquid is above the level of the ends 36 and 38 then energy will be lost from the Lamb wave propagating in the wall 10 due to mode conversion to compression waves in the liquid, and consequently the Lamb wave detected by the receiver transducer 20 will have an amplitude B which is less than the amplitude A. Hence the difference between A and B is an indication of the presence of the liquid at the level of the ends 36 and 38 of the strips 30 and 34. The signal detector 24 receives signals from the receiver transducer 20 related to the amplitude of the detected Lamb wave, and is arranged to provide an indication when the amplitude of the signal received falls below a selected threshold value chosen in comparison with the amplitude of the signal when the detected wave has amplitude A. (If the container 12 is a pipe, the signal detector 24 may incorporate a time gate so that Lamb waves which travel the opposite direction around the wall 10 of the pipe are not detected).

The difference between A and B must be large enough to provide a sufficient signal-to-noise ratio for the sensor. This can be accomplished by an appropriate selection of the distance between the end 36 of the strip 30 and the end 38 of the strip 34 and of the frequency at which the signal generator 18 causes the transmitter transducer 14 to oscillate. The frequency of the signal applied to the transmitter transducer 14, and the thickness of the strip 30 or of the wall 10, together determine the modes of Lamb wave generated by the transmitter transducer 14 in the strip 30, and propagated through the wall 10 of the container. For optimum generation of Lamb waves in the wall 10, the thickness of the strip 30 is less than half of the wavelength of the Lamb wave generated in the wall 10.

A storage tank for containing a liquid may be provided with a plurality of such sensors at different levels on the outside of the wall of the tank, so that an indication of discrete changes of the liquid level in the tank may be obtained.

The stainless steel strips 30 and 34 may be of any convenient length up to several meters, and so the transducers 14 and 20 may be situated remote from the container 12.

It has been found that optimum attenuation of the Lamb waves by mode conversion into the liquid occurs when the propagation distance in the wall of the container is at least 100 mm. Consequently if the sensor is to be applied to a pipe of diameter for example 25 mm, then the points at which the ends 36 and 38 of the strips 30 and 34 are attached to the pipe are preferably separated by a distance of 100 mm along the length of the pipe, the ends 36 and 38 being in planes perpendicular to the longitudinal axis of the pipe and being cut concavely to fit onto the outside of the pipe, rather than being at the same horizontal level as in the sensor of FIG. 1.

The sensor of FIG. 1 may be used as described above to detect whether the surface of a liquid is above or below the portion of the wall 10 to which the ends 36 and 38 of the strips 30 and 34 are attached, because there is a relatively large difference between the amplitudes A and B. If the container 12 were to contain two immiscible liquids, there would again be a difference in amplitude of the Lamb wave detected by the receiver transducer 20 depending on which liquid is adjacent to the portion of the wall 10, because the attenuation of the Lamb wave propagating through the wall 10 depends upon the acoustic impedance of the fluid adjacent to the wall 10, which generally can be expected to be different for different liquids. This difference in amplitude is however less than that between A and B, and may be masked by variations in the sensitivity of the signal detector 24.

Figure 2:
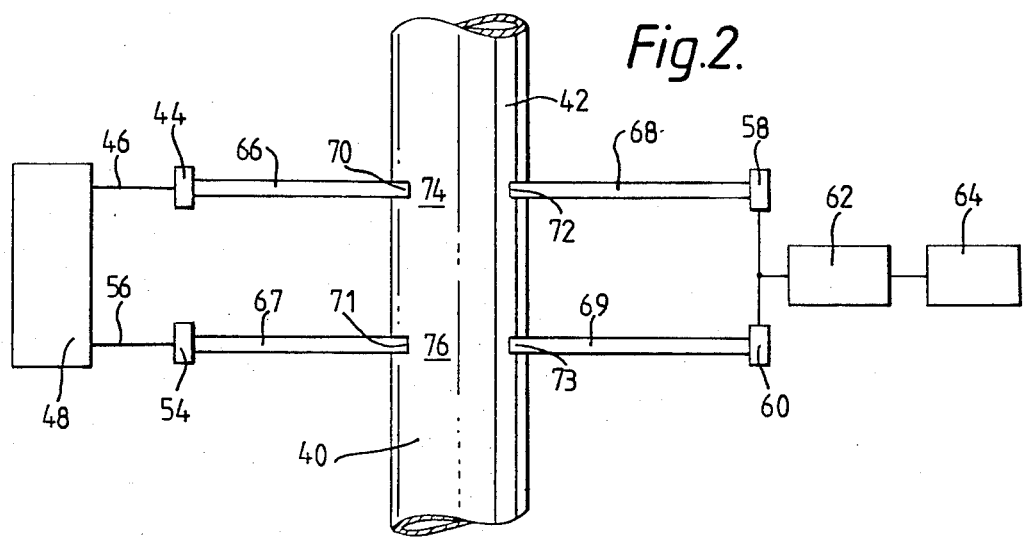
FIG. 2 shows diagrammatically an alternative liquid interface sensor embodying the invention.

Referring to FIG. 2, an alternative liquid interface sensor is shown attached to the outside of a wall 40 of a container 42 (shown as a pipe) containing two immiscible liquids. The sensor comprises an upper transducer 44 connected by an electric cable 46 to a signal generator 48, a lower transmitter transducer 54 connected by an electric cable 56 to a different terminal of the signal generator 48; and an upper receiver transducer 58 and a lower receiver transducer 60 connected to a common input of an amplifier 62 linked to a signal analyser 64. Each transducer 44, 54, 58 or 60 is acoustically coupled to the wall 40 by a respective stainless steel strip 66, 67, 68 or 69, 25 mm wide and 1.5 mm thick, being attached to an end of the strip. The other ends 70 and 72 of the strips 66 and 68 respectively are both welded to the wall 40 at the same horizontal level so as to define an upper portion 74 of the wall 40 between them; while the other ends 71 and 73 of the strips 67 and 69 respectively are both welded to the wall 40 at the same horizontal level as each other so as to define a lower portion 76 of the wall 40 between them, the level of the lower portion 76 being sufficiently far below the level of the upper portion 74 that Lamb waves propagating through the upper portion 74 of the wall 40 produce no detectable effect at the lower portion 76, and vice versa.

In operation of the sensor of FIG. 2, the signal generator 48 energises the upper transmitter transducer 44 and the lower transmitter transducer 54 alternately. When each is energised it causes Lamb waves to propagate along the respective strip 66 or 67, generating Lamb waves in the upper portion 74 or the lower portion 76 of the wall 40 respectively, which generate Lamb waves in the respective strip 68 or 69, which are detected by the upper or lower receiver transducer 58 or 60 respectively. The amplifier 62 thus receives signals alternately via the upper portion 74 or the lower portion 76 of the wall 40; and the signal analyser 64 determines the ratio of these signals.

If the interface between the two liquids is above the upper portion 74 then both signals will have the same amplitude, and the ratio will be 1. If the interface lies between the upper portion 74 and the lower portion 76 then the two signals will have different amplitudes, depending on the attenuation due to the liquids and hence on the acoustic impedances of the liquids, and so the ratio will differ from one. For example if the liquids are water and kerosene, the ratio will be 2:3. If the interface lies below the lower portion 76 then again both signals will have the same amplitude, and the ratio will again be 1. Thus the value of the ratio of the signal amplitudes indicates whether or not the interface lies between the limits set by the position of the upper portion 74 and the lower portion 76 of the wall 40. If the interface rises or falls to be outside these limits, then the signal analyser 64 detects which signal underwent a change, and hence indicates whether the interface has risen or fallen.

It will be appreciated that the absolute values of the signals received by the signal analyser 64 do not affect the operation of the sensor, and so the sensor is unaffected by variations in the gain of the amplifier 62. However it is preferable that the signal analyser 64 should monitor the absolute values of the received signals so that rapid or large changes may be used to trigger an alarm—such changes might for example be due to a change in the acoustic coupling between a transducer and the corresponding strip.

As a further precaution against failure of the sensor, a second set of upper and lower receiver transducers (not shown), with a common amplifier and signal analyser (not shown) may be provided, acoustically coupled to the wall 40 by strips (not shown), the upper strip being welded to the wall 40 as far to the left of the end 70 as the end 72 is to the right (as shown), and the lower strip being welded as far to the left of the end 71 as the end 73 is to the right. A Lamb wave propagating in the strip 66 or 67 causes Lamb waves to propagate in both directions around the wall 40, so the signals received by the second set of receiver transducers should be the same as those received by the transducers 58 and 60. Thus the indications provided by the second signal analyser (not shown) may be used as a check on the operation of the sensor, as they should duplicate the indications provided by the signal analyser 64.

Figure 3:
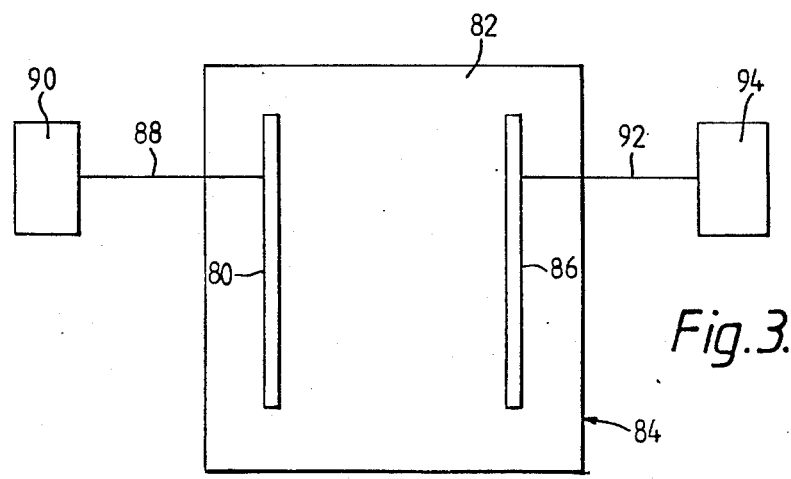
FIG. 3 shows diagrammatically a third form of liquid interface sensor.

In FIG. 3 is shown another liquid interface sensor including a long transmitter transducer 80 attached to a wall 82 of a container 84, extending a distance approximately equal to the range of liquid levels the sensor is to indicate, and a long receiver transducer 86 of the same length as and parallel to the transmitter transducer 80, also attached to the wall 82. The transmitter transducer 80 is connected by an electric cable 88 to a signal generator 90, and the receiver transducer 86 is connected by an electric cable 92 to a signal detector 94.

When the signal generator 90 is energised, the transmitter transducer 80 causes a Lamb wave, with wavefronts parallel to the transducer 80, to propagate through the wall 82 of the container 84. The Lamb wave is therefore in phase throughout the length of the receiver transducer 86. A corresponding signal is sent by the receiver transducer 86 to the signal detector 94. If the level of the liquid in the container 84 is below the level of the bottom ends of the transducers 80 and 86 then the Lamb wave is not attenuated by mode conversion into compression waves in the liquid and the signal has an amplitude P, whereas if the level of the liquid is above the top ends of the transducers 80 and 86 the Lamb wave is attenuated by mode conversion into compression waves in the liquid throughout the length of the wavefronts, and the signal has an amplitude Q. For intermediate liquid levels a part of the wavefront of the Lamb waves is attenuated by mode conversion into compression waves in the liquid and the signal amplitude lies between the values P and Q. Although the relationship between signal amplitude and liquid level has been found to be not exactly linear throughout the length of the transducers 80 and 86, the sensor may be calibrated to provide an indication of liquid level throughout the length of the transducers 80 and 86.

The transducers 80 and 86 may be electromagnetic transducers or piezoelectric transducers, and each transducer 80 and 86 may consist of a plurality of short transducers laid end to end, and electrically connected so as to oscillate in phase when they are energised simultaneously.

Figure 4:
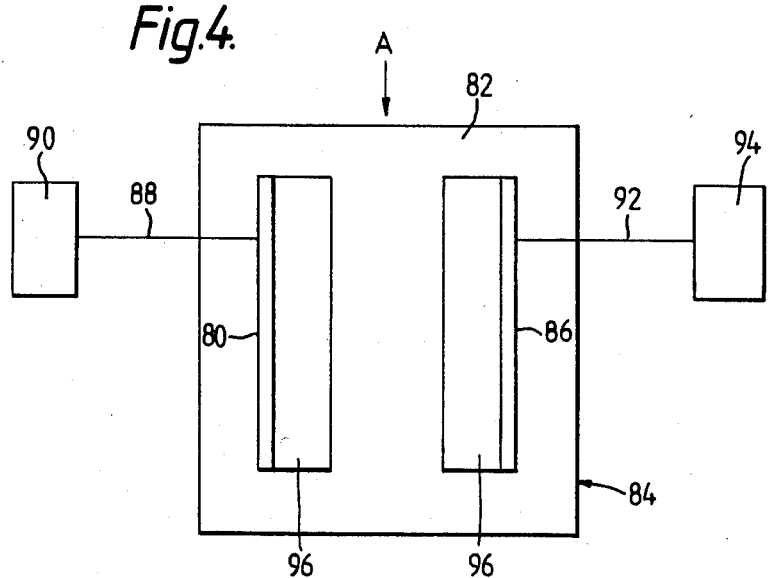
FIG. 4 shows diagrammatically a modified form of the sensor of FIG. 3.
Figure 5:
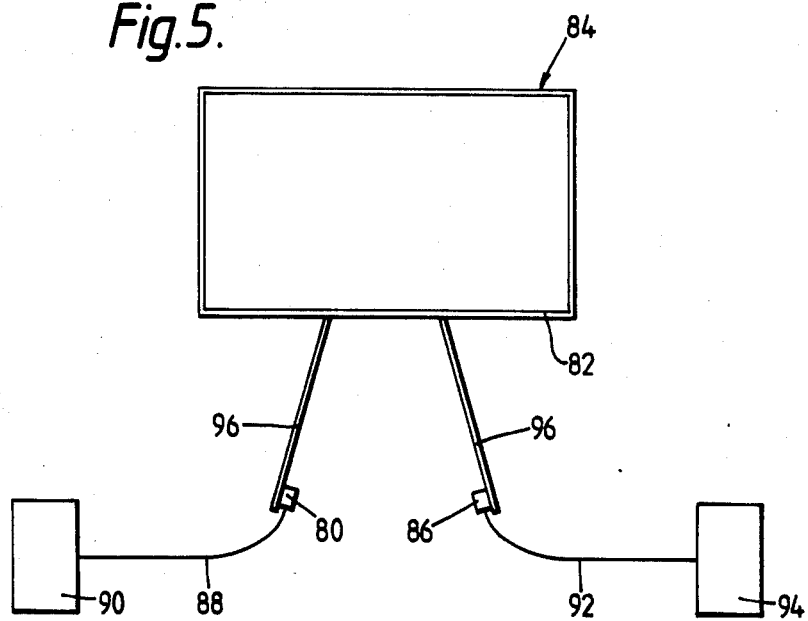
FIG. 5 shows a view in the direction of arrow A of FIG. 4.

Although the transducers 80 and 86 have been described as attached directly to the wall 82 it will be appreciated that alternatively as shown in FIG. 4 and FIG. 5, they may be acoustically coupled thereto by waveguides in the form of rectangular stainless steel sheets 96 about 1.5 mm thick, of breadth equal to the length of the transducer, and of sufficient length that the transducers are unlikely to be damaged by heat or radiation from the container.

We claim:

1. A method for detecting an interface of a liquid in a container comprising, causing Lamb waves to propagate through a portion of a wall of the container, receiving the Lamb waves after they have propagated through the portion of the wall, and detecting the liquid interface in response to the amplitude of the received Lamb waves, wherein the Lamb waves are transmitted to and from the portion of the wall as Lamb waves propagating along respective strip waveguides, only an end of each waveguide contacting the wall thereby separating transmitting and receiving transducers of the propagated lamb waves from the wall of the container.

2. A sensor to detect an interface of a liquid in a container for containing the liquid, comprising a first ultrasonic transducer situated outside the container and arranged to cause Lamb waves of predetermined wavelength to propagate through a portion of a wall of the container, a second ultrasonic transducer situated outside the container and arranged to detect Lamb waves propagating through the portion of the wall and to produce an electrical signal related to the amplitude thereof, and indicating means responsive to the electrical signal from the second transducer to provide an indication of an interface of the liquid within the container, wherein the first ultrasonic transducer and the second ultrasonic transducer are acoustically coupled to the wall by respective strip waveguides along which Lamb waves propagate, only an end of each waveguide contacting the wall thereby separating said transducers from the wall of the container.

3. A sensor as claimed in claim 2, further comprising a third ultrasonic transducer situated outside the container for causing Lamb waves of predetermined wavelength to propagate through a second portion of the wall lower than the first-mentioned portion; a fourth ultrasonic transducer situated outside the container for detecting Lamb waves propagating through the second portion of the wall and for producing an electrical signal related to the amplitude thereof; and means for exciting the first and the third ultrasonic transducer; the third ultrasonic transducer and the fourth ultrasonic transducer being acoustically coupled to the wall by respective strip waveguides along which Lamb waves propagate, only an end of each waveguide contacting the wall; and the indicating means being responsive to the signals from both the second and the fourth ultrasonic transducer for providing an indication of the interface.

4. A sensor as claimed in claim 2 wherein the thickness of each strip waveguide is less than a tenth of the breadth thereof.

5. A sensor as claimed in claim 2 wherein the thickness of each strip waveguide is less than half the said wavelength of the Lamb waves which are to propagate through the respective portion of the wall.

6. A sensor as claimed in claim 2, wherein the strip waveguides are coupled to the wall along parallel lines, each line extending vertically through a distance equal to an expected variation in the interface of the liquid.

7. A sensor as claimed in claim 3 wherein the thickness of each strip waveguide is less than a tenth of the breadth thereof.

8. A sensor as claimed in claim 3 wherein the thickness of each strip waveguide is less than half the said wavelength of the Lamb waves which are to propagate through the respective portion of the wall.

* * * * *